(12) United States Patent
Campbell et al.

(10) Patent No.: US 10,828,371 B2
(45) Date of Patent: Nov. 10, 2020

(54) MULTIFUNCTIONALIZED BIOACTIVE POLYCAPROLACTONE

(71) Applicant: International Business Machines Corporation, Armonk, NY (US)

(72) Inventors: Eric J. Campbell, Rochester, MN (US); Sarah K. Czaplewski-Campbell, Rochester, MN (US); Brandon M. Kobilka, Tucson, AZ (US); Jason T. Wertz, Peasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/806,433

(22) Filed: Nov. 8, 2017

(65) Prior Publication Data

US 2019/0134209 A1  May 9, 2019

(51) Int. Cl.
| | |
|---|---|
| *C08G 63/685* | (2006.01) |
| *A61K 47/59* | (2017.01) |
| *C08G 63/682* | (2006.01) |
| *C08G 63/82* | (2006.01) |

(52) U.S. Cl.
CPC .......... *A61K 47/593* (2017.08); *C08G 63/682* (2013.01); *C08G 63/685* (2013.01); *C08G 63/6822* (2013.01); *C08G 63/6852* (2013.01); *C08G 63/823* (2013.01)

(58) Field of Classification Search
None
See application file for complete search history.

(56) References Cited

U.S. PATENT DOCUMENTS

| | | | | |
|---|---|---|---|---|
| 4,353,832 A | * | 10/1982 | Lecloux | C07C 51/285 549/263 |
| 5,362,919 A | * | 11/1994 | Costello | C07B 39/00 568/601 |
| 5,721,329 A | | 2/1998 | Fujiwa et al. | |
| 8,470,958 B1 | | 6/2013 | Turos et al. | |
| 8,927,682 B2 | | 1/2015 | Baker et al. | |
| 2010/0137206 A1 | | 6/2010 | Lavasanifar et al. | |
| 2018/0320077 A1 | * | 11/2018 | Campbell | C09K 21/12 |

FOREIGN PATENT DOCUMENTS

| | | |
|---|---|---|
| CN | 101696267 A | 4/2010 |
| CN | 104448260 A | 3/2015 |
| CN | 106084156 A | 11/2016 |
| EP | 2 730 604 A2 | 5/2014 |

OTHER PUBLICATIONS

Yan, Jinliang et al, "Novel poly(e-caprolatone)s bearing amino groups: synthesis, characterization and biotinylation." React. and Funct. Polym. (2010) 70 p. 400-407.*
Tallawi, Marwa et al, "Strategies for the chemical and biological functionalization of scaffolds for cardiac tissue engineering: a review." J. R. Soc. Interface (2015) 12 (20150254).*
Lou, Xudong et al, "Controlled synthesis and chemical modification of unsaturated alophatic (co) polyesters based on 6, 7-dihydro-2 (3H)-oxepinone." J. Poly. Sci. A (2002) 40 p. 2286-2297.*
Mergler, M. and Durieux, J. P.; "The bachem practice of spps.", Bachem sales literature (2005).*
Peixoto, Luciana et al, "Synthesis of poly(vinyl alcohol) and/or poly(vinyl acetate) particles with spherical morphology and core-shell structure and its use in vascular embolization." Macromol. Symp. (2006) 243 p. 190-199.*
Keul, Helmut and Moller, Martin; "Synthesis and degradation of biomecial materials based on linear and star shaped polyglycidols." J. Polym. Sci. A (2009) 47 p. 3209-3231.*
Saadaoui, Asma et al; "New biosourced aa and ab monomers from 1, 4:3, 6-dianhydrohexaitols, isosorbide, isomannide, and isoidide." Des. Mono. Polym. (2017) 20 (1) p. 221-233, available Sep. 2016.*
Chen, Tingting et al, "Design and fabrication of functional polycaprolactone." e-Polymers (2015) 15(1) p. 3-13.*
Delaittre et al., "Chemical approaches to synthetic polymer surface biofunctionalization for targeted cell adhesion using small binding motifs," Soft Matter, 2012, 8, pp. 7323-7347, The Royal Society of Chemistry 2012. DOI: 10.1039/c2sm07407a.
Noga, D., Synthesis of Functional Lactide Copolymers for Use in Biomedical Applications, Dissertation in Partial Fulfillment of the Requirements for the Degree Doctor of Philosophy, Georgia Institute of Technology, Aug. 2008, 219 pages.
Tallawi et al., "Strategies for the chemical and biological functionalization of scaffolds for cardiac tissue engineering: a review," Journal of the Royal Society Interface, Jul. 2015, vol. 12, Issue 108, pp. 1-24, The Royal Society Publishing. DOI: 10.1098/rsif.2015.0254.
Woodruff et al., "The return of a forgotten polymer— Polycaprolactone in the 21st century," Progress in Polymer Science, Oct. 2010, vol. 35, Issue 10, pp. 1-40, Elsevier. DOI: 10.1016/tprogpolymsci.2010.04.002.

* cited by examiner

*Primary Examiner* — Fred H Reynolds
(74) *Attorney, Agent, or Firm* — Kelsey M. Skodje (57) ABSTRACT

A multifunctionalized polycaprolactone polymer, a process for forming a multifunctionalized polycaprolactone polymer, and an article of manufacture comprising a material containing a multifunctionalized polycaprolactone polymer are disclosed. The multifunctionalized polycaprolactone polymer includes at least two functional groups. The process of forming the multifunctionalized polycaprolactone polymer includes forming a caprolactone monomer having at least two functional groups, and polymerizing the caprolactone monomer. Further, the article of manufacture includes a polycaprolactone polymer having at least two functional groups.

15 Claims, 12 Drawing Sheets
Specification includes a Sequence Listing.

Polycaprolactone
204

208

L and L' =  -NH$_2$ and -NH$_2$,
            -NH$_2$ and -OH, or
            -NH$_2$ and -H.

M, M'', and M'' = -H, -H, and -H;
            -NH$_2$, -H, and -H;
            -NH$_2$, -NH$_2$, and -H;
            -NH$_2$, -OH, and -H; or
            -NH$_2$, -NH$_2$, and -NH$_2$

1. NaN$_3$, DMF, 75 °C
2. PPh$_3$, dioxane, reflux

438

X, X', and X" =  -H, -H, and -H (412);
-Br, -H, and -H (416);
-Br, -Br, and -H (428); or
-Br, -Br, and -Br (432)

M, M', and M" =  -H, -H, and -H;
-NH$_2$, -H, and -H;
-NH$_2$, -NH$_2$, and -H; or
-NH$_2$, -NH$_2$, and -NH$_2$

↓ Sn(Oct)$_2$

↓ Sn(Oct)$_2$

↓ NH₃, catalyst

604

↓ Sn(Oct)₂

Biomolecule A ↓

704

Biomolecule B ↓

MULTIFUNCTIONALIZED BIOACTIVE POLYCAPROLACTONE

BACKGROUND

SEQUENCE LISTING

A text file containing a sequence listing is incorporated by reference herein in its entirety. The name of the text file is AUS820160965US01_Text_File, the date of creation of the text file is Sep. 24, 2018, and the size of the text file in bytes is 1.03 KB.

The present disclosure relates to polycaprolactone and more specifically to multifunctionalized polycaprolactone.

Polycaprolactone ((1,7)-polyoxepan-2-one) is a biodegradable polymer that was developed in the 1930s, and has been used in a variety of applications since then. Polycaprolactone can be blended with other materials to impart solvent or water resistance, increase biodegradability, act as a plasticizer, etc. Further, polycaprolactone has been approved for use in the human body by the Food and Drug Administration (FDA). Polycaprolactone is prepared by ring-opening polymerization of ε-caprolactone with a variety of catalysts, such as anionic, cationic, and coordination catalysts.

SUMMARY

Various embodiments are directed to a multifunctionalized polycaprolactone polymer, a process for forming a multifunctionalized polycaprolactone polymer, and an article of manufacture containing a multifunctionalized polycaprolactone polymer. The multifunctionalized polycaprolactone has a first and a second functional group, and can also have a third, fourth, and/or fifth functional group. Further, the multifunctionalized polycaprolactone polymer can have a first, second, and/or third hydrogen atom. In some embodiments, the first functional group and the second functional group are amino groups. Further, the third functional group, the fourth functional group, and the fifth functional group can be amino groups. Additionally, in some embodiments, the second functional group is a hydroxyl group. The multifunctionalized polycaprolactone polymer is formed in a process that includes polymerizing a multifunctionalized caprolactone polymer.

The process of forming the multifunctionalized polycaprolactone polymer comprises forming a caprolactone monomer having at least two functional groups, and polymerizing the caprolactone monomer. In some embodiments, the at least two functional groups are amino groups. Further, the at least two functional groups can be bromine groups, which can be replaced by amino groups. Additionally, the multifunctionalized polycaprolactone polymer can be reacted with a bioactive compound. Examples of bioactive compounds that can participate in this reaction can include RGD peptides, YIGSR peptides (SEQ ID NO: 1), IKVAV peptides (SEQ ID NO: 2) fibronectin-derived REDV peptides (SEQ ID NO: 3) collagen I mimetic DGEA peptides (SEQ ID NO: 4), osteopontin-derived SVVYGR peptides (SEQ ID NO: 5) elastin-derived VAPG peptides (SEQ ID NO: 6), a peptidomimetic, galactose, lactose, vascular endothelial growth factor, fibronectin domain III 12-14, EC2 cells, bone morphogenetic protein 2, calcium phosphate, dexamethasone, glycerolphosphate, transforming growth factor beta, basic fibroblast growth factor, SH3 domain-containing proteins, SH3-binding peptides, and nerve growth factor, etc.

The article of manufacture comprises a multifunctionalized polycaprolactone polymer which has a first and a second functional group, and can also have a third, fourth, and/or fifth functional group. Further, the multifunctionalized polycaprolactone polymer can have a first, second, and/or third hydrogen atom. In some embodiments, at least one bioactive compound is bound to the polycaprolactone polymer. Examples of bioactive compounds that can be bound can include RGD peptides, YIGSR peptides (SEQ ID NO: 1), IKVAV peptides (SEQ ID NO: 2), fibronectin-derived REDV peptides (SEQ ID NO: 3), collagen I mimetic DGEA peptides (SEQ ID NO: 4), osteopontin-derived SVVYGR peptides (SEQ ID NO: 5), elastin-derived VAPG peptides (SEQ ID NO: 6), a peptidomimetic, galactose, lactose, vascular endothelial growth factor, fibronectin domain III 12-14, EC2 cells, bone morphogenetic protein 2, calcium phosphate, dexamethasone, glycerolphosphate, transforming growth factor beta, basic fibroblast growth factor, SH3 domain-containing proteins, SH3-binding peptides, and nerve growth factor, etc. Further, the article of manufacture can be a tissue scaffold or a drug delivery capsule.

DETAILED DESCRIPTION

Polycaprolactone (1,7-polyoxepan-2-one) is a biodegradable polymer with wide ranging applications. It was developed in the 1930s, and approved for use in humans by the Food and Drug Administration (FDA) in the 1980s. Polycaprolactone's biodegradability and FDA approval make it suitable for biomedical applications. Further, polycaprolactone has other properties that allow it to have varied applications. For example, polycaprolactone has good solubility in a number of solvents (e.g., chloroform, dichloromethane, carbon tetrachloride, benzene, toluene, cyclohexanone, 2-nitropropane, acetone, 2-butanone, ethyl acetate, dimethylformamide, acetonitrile, etc.), a low melting point (59° C.-64° C.), and an ability to easily blend with many other materials (e.g., cellulose propionate, cellulose acetate butyrate, polylactic acid, and polylactic acid-co-glycolic acid, etc.). Blending or copolymerizing polycaprolactone with materials such as these can impart solvent or water resistance, increase biodegradability, increase plasticity, manipulate the rate of polymer degradation, etc.

Polycaprolactone is prepared by ring-opening polymerization of ε-caprolactone (referred to herein as caprolactone) with an appropriate catalyst, such as an anionic, cationic, or coordination catalyst. Block and random copolymers of polycaprolactone can be produced by polymerizing caprolactone (2-oxepanone) along with other monomers (e.g., ethylene oxide, polyvinylchloride, chloroprene, polyethylene glycol, polystyrene, diisocyanates (urethanes), tetrahydrofuran, diglycolide, dilactide, δ-valerolactone, substituted caprolactones, 4-vinyl anisole, styrene, methyl methacrylate, vinyl acetate, etc.). Herein, polycaprolactone and its copolymers are referred to as polycaprolactone polymers.

Polycaprolactone polymers can have functional groups (e.g., hydroxyl groups, amino groups, carboxylic acid groups, halide groups, thiol groups, etc.). Functional groups can adjust the properties of the polymers and/or participate in reactions. For example, various molecules can be attached to polycaprolactone by binding to its functional groups. Functional groups are generally added in additional reactions and/or processing steps, or by copolymerizing caprolactone with another functionalized monomer. In biomedical applications, the molecules bound to functional groups on polycaprolactone polymers are often bioactive compounds (i.e., compounds that have an effect on a living organism). Examples of bioactive compounds that can be attached to polycaprolactone can include biomolecules that are involved in drug delivery, cell adhesion, vascular tissue engineering, bone tissue engineering, neural tissue engineering, etc. These compounds are discussed in greater detail below. Polycaprolactone polymers with or without functional groups can also be used in vehicles for drug delivery, sutures, wound dressings, contraceptive devices, orthopedic devices, synthetic tissues, tissue regrowth scaffolds, etc.

However, the number and variety of molecules that can be attached to the polycaprolactone polymer are limited by the additional processing steps and/or copolymerization with additional functionalized monomers. These processing steps and additional monomers can add complexity to the production of the polymers, and can affect properties of the polymers in undesirable ways (e.g., by changing their strength, elasticity, biodegradability, compatibility with other materials, etc.).

The polycaprolactone polymers disclosed herein reduce the need for post-polymerization processing steps. These polycaprolactone polymers have multiple functional groups that provide variable active sites for binding additional molecules, and are produced without requiring additional post-polymerization steps or copolymerization. Instead, the disclosed polycaprolactone polymers are produced from caprolactone monomers having at least two functional groups. The number and identity of the functional groups on the polycaprolactone polymer is tunable, and determined by the number and identity of functional groups on the starting caprolactone monomer.

Figure 1:
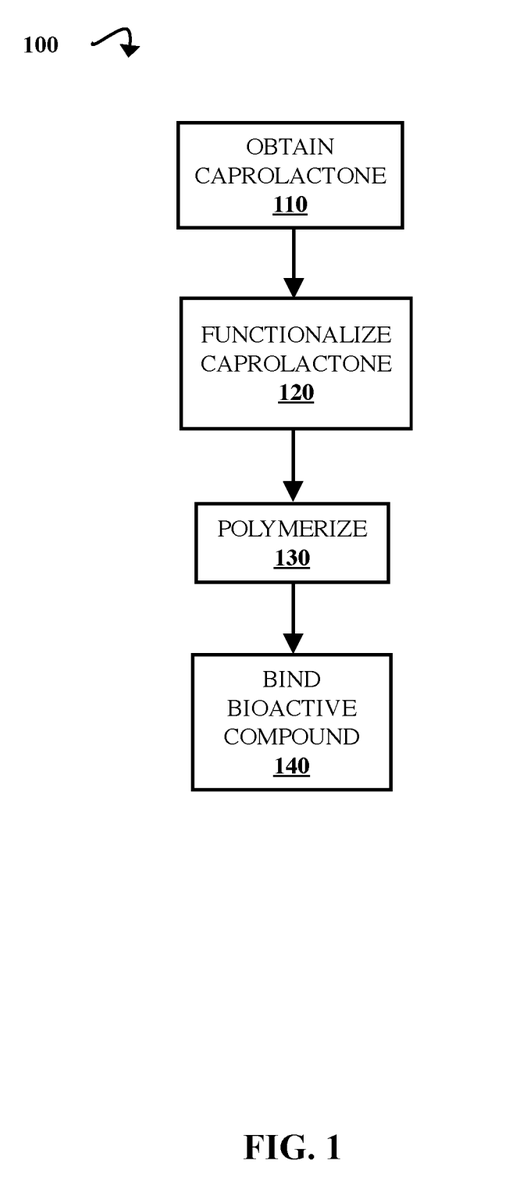
FIG. 1 is a flow diagram illustrating a process of binding a bioactive compound to a multifunctionalized polycaprolactone polymer, according to some embodiments of the present disclosure.

FIG. 1 is a flow diagram illustrating a process 100 of binding a bioactive compound to a multifunctionalized polycaprolactone polymer, according to some embodiments of the present disclosure. Process 100 begins with the obtainment of caprolactone. This is illustrated at step 110. Caprolactone is produced on an industrial scale, and is commercially available, though it can also be synthesized in situ. Caprolactone is produced by Baeyer-Villiger oxidation of cyclohexanone with peracetic acid. Baeyer-Villiger oxidation is a reaction that uses peroxyacids or peroxides as oxidants to produce an ester from a ketone or a lactone from a cyclic ketone.

Process 100 continues with reactions to produce a multifunctionalized caprolactone. This is illustrated at step 120. The multifunctionalized caprolactone is a caprolactone derivative with functional groups (e.g., hydroxyl or amino functional groups). These functional groups are capable of binding to substituents on other molecules, such as bioactive molecules. The multifunctionalized caprolactone can have two, three, four, or five functional groups, depending on the reaction conditions under which it is produced. The syntheses and structures of these caprolactones are discussed in greater detail with regard to FIGS. 3A-4B, 5A, and 6.

The multifunctionalized caprolactone is polymerized to form a multifunctionalized polycaprolactone polymer. This is illustrated at step 130. The polymerization reaction is a ring-opening polymerization. The ring-opening polymerization is catalyzed by stannous octoate (tin(II)-ethylhexanoate, $Sn(Oct)_2$) in some embodiments. However, the ring-opening polymerization can also be carried out with other catalysts. Examples of these catalysts can include anionic catalysts, cationic catalysts, and coordination catalysts. Further, the anionic, cationic, and coordination catalysts can be metal-based, organic-based, enzyme-based, etc. In some embodiments, subsequent reactions are carried out on the polymer to attach additional functional groups. The average molecular weight of the polycaprolactone polymers varies from about 3,000 g/mol to about 80,000 g/mol.

The polymerization can also involve the addition of cross-linkers, chain-extenders, and/or monomers other than the multifunctionalized caprolactone prepared in step 120. For example, non-functionalized caprolactone can be added in order to adjust the total number of functional groups on the polymer chain. Other examples of added monomers can include ethylene oxide, polyvinylchloride, chloroprene, polyethylene glycol, polystyrene, diisocyanates (urethanes), tetrahydrofuran, diglycolide, dilactide, δ-valerolactone, substituted caprolactones, 4-vinyl anisole, styrene, methyl methacrylate, vinyl acetate, etc. The ratios and identities of monomers affect the properties of the resulting polycaprolactone polymer (e.g., strength, elasticity, biodegradability, compatibility with other materials, number of active sites, etc.). In some embodiments, the active sites provided by the multifunctionalized caprolactone monomer can be reacted with additional small molecules that provide alternative functional groups (e.g., carboxylic acid, aldehydes, allyls, alkynyls, esters, thiols, etc.) at the active sites. Further, the polycaprolactone polymers produced in step 130 can be blended with other polymers. This is discussed in greater detail with respect to FIG. 7.

Bioactive compounds are then attached to the multifunctionalized polycaprolactone polymer. This is illustrated at step 140. The bioactive compounds bind to active sites (i.e., functional groups) on the multifunctionalized polycaprolactone. Examples of bioactive compounds that will bind to the active sites can include deoxyribonucleic acid (DNA), ribonucleic acid (RNA), proteins, peptides, antibiotics or other drugs, etc.

Further examples of bioactive compounds that will bind to these active sites can include compounds that promote cell adhesion, such as short peptides (e.g., Arg-Gly-Asp (RGD), Tyr-Ile-Gly-Ser-Arg (YIGSR) (SEQ ID NO: 1), Ile-Lys-Val-Ala-Val (IKVAV) (SEQ ID NO: 2), fibronectin-derived Arg-Glu-Asp-Val (REDV) (SEQ ID NO: 3), collagen I mimetic Asp-Gly-Glu-Ala (DGEA) (SEQ ID NO: 4), osteopontin-derived Ser-Val-Val-Tyr-Gly-Leu-Arg (SV-VYGR) (SEQ ID NO: 5), elastin-derived Val-Ala-Pro-Gly (VAPG) (SEQ ID NO: 6), etc.), derivatives or combinations of short peptides, peptidomimetics, carbohydrates (e.g., galactose and lactose), etc. Examples of bioactive compounds that will bind to the active sites can also include compounds used in vascular tissue engineering (e.g., vascular endothelial growth factor (VEGF), fibronectin (FN) domain III 12-14, EC2 cells, etc.), bone tissue engineering (e.g., bone morphogenetic protein 2 (BMP2), FN domain III 12-14, calcium phosphate ($Ca_3(PO_4)_2$), dexamethasone, glycerolphosphate, transforming growth factor beta (TGF-β), etc.) or neural tissue engineering (e.g., basic fibroblast growth factor (bFGF), Src homology 3 (SH3) domain-containing proteins, SH3-binding peptides, nerve growth factor (NGF), etc.).

Figure 2:
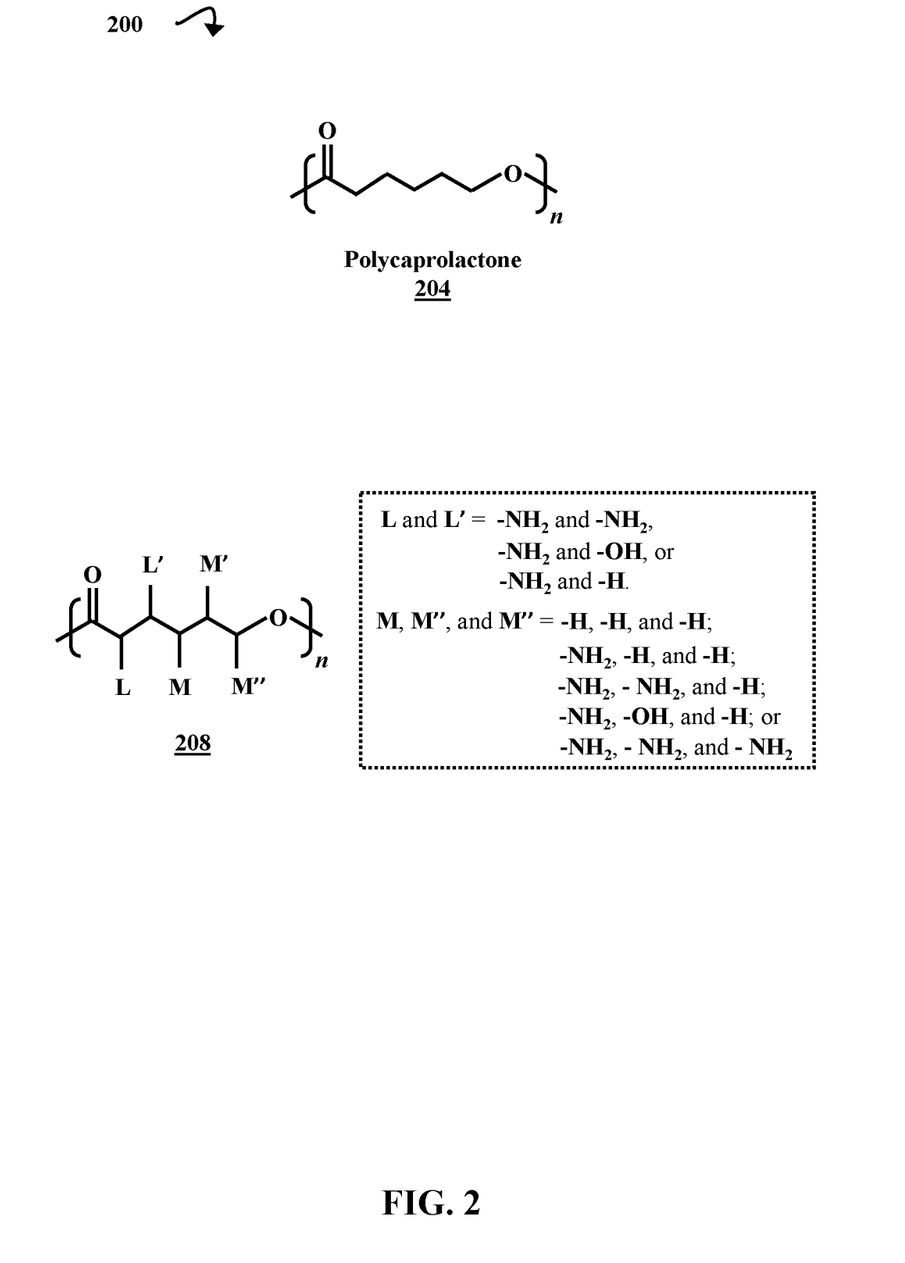
FIG. 2 is a diagrammatic representation of the molecular structures of non-functionalized polycaprolactone and a generic example of a multifunctionalized polycaprolactone

FIG. 2 is a diagrammatic representation of the molecular structures of non-functionalized polycaprolactone 204 and a generic example of the multifunctionalized polycaprolactone formed in step 130. The multifunctionalized polycaprolactone 208 has variable substituents that can include amino groups (—$NH_2$), hydroxyl groups (—OH), and hydrogen atoms (—H). These substituents are represented by L, L', M, M', and M". The multifunctional polycaprolactone polymer 208 has at least two functional groups (e.g., —$NH_2$ and/or —OH). The substituents L and L' can be —$NH_2$ and —$NH_2$ or —$NH_2$ and —OH, respectively. Further, M and M" can be amino groups or hydrogen atoms, and M' can be an amino group, hydroxyl group, or hydrogen atom. The number and identity of the substituents is determined by the multifunctionalized caprolactone monomer starting material. When a position is a hydrogen atom, the position is referred to as "non-functionalized" herein. The multifunctionalized caprolactone monomers are discussed in greater detail below.

Figure 3A:
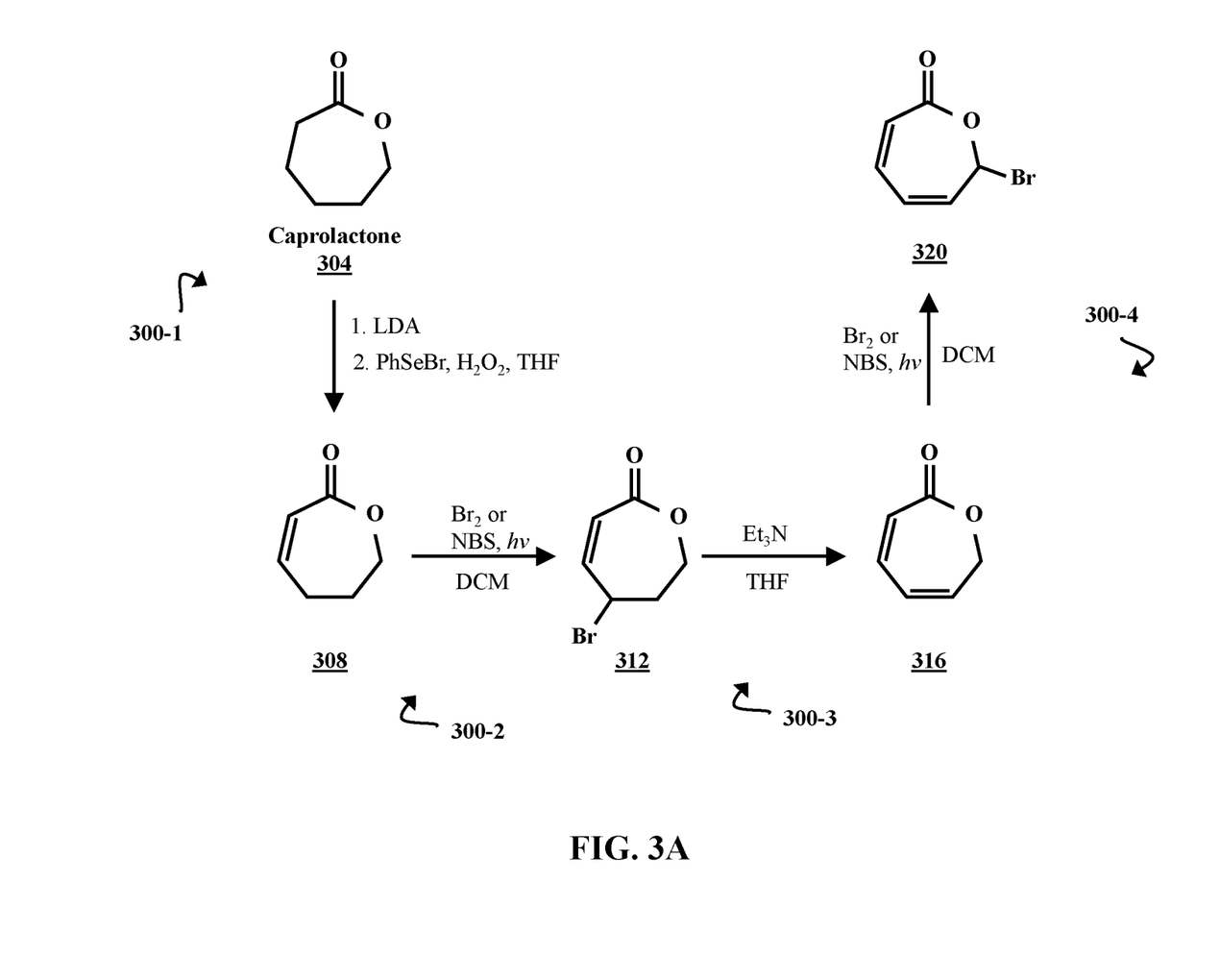
FIG. 3A is a chemical reaction diagram illustrating processes of synthesizing four unsaturated caprolactones, according to some embodiments of the present disclosure.

FIG. 3A is a chemical reaction diagram illustrating processes 300-1, 300-2, 300-3, and 300-4 of synthesizing four unsaturated caprolactones 308, 312, 316, and 320, according to some embodiments of the present disclosure. In process 300-1, caprolactone 304 is combined with lithium diisopropylamide (LDA) to produce an enolate (not shown). In a second step, the enolate undergoes a selenoxide elimination reaction with phenylselenyl bromide (PhSeBr) and hydrogen peroxide ($H_2O_2$) in a tetrahydrofuran (THF) solution. The selenoxide elimination produces α,β-unsaturated caprolactone 308. Phenylselenyl bromide and hydrogen peroxide are the selenylating agent and oxidizing agent, respectively. However, other selenylating agents (e.g., diphenyl selenide, benzeneselenyl chloride, sodium benzeneselenolate, trimethylsilyl phenyl selenide, etc.) are used in some embodiments.

In process 300-2, the α,β-unsaturated caprolactone 308 is combined with bromine ($Br_2$) or N-bromosuccinimide (NBS) in a dichloromethane (DCM) solution, and exposed to photons (hv). This triggers a radical bromination reaction, which produces a bromo-caprolactone 312. In process 300-3 the bromine substituent on the bromo-caprolactone 312 is eliminated in a reaction with a hindered base, triethylamine ($Et_3N$), in a THF solution. The bromine elimination produces a di-unsaturated caprolactone 316. It should be noted that hindered bases other than triethylamine (e.g., t-butoxide, diisopropylamine, dimethylpyridine, etc.) are used in some embodiments. A second radical bromination is carried out in process 300-4. This radical bromination adds a bromine substituent to the di-unsaturated caprolactone 316 under substantially the same conditions as process 300-2, and forms a di-unsaturated bromo-caprolactone 320.

Figure 3B:
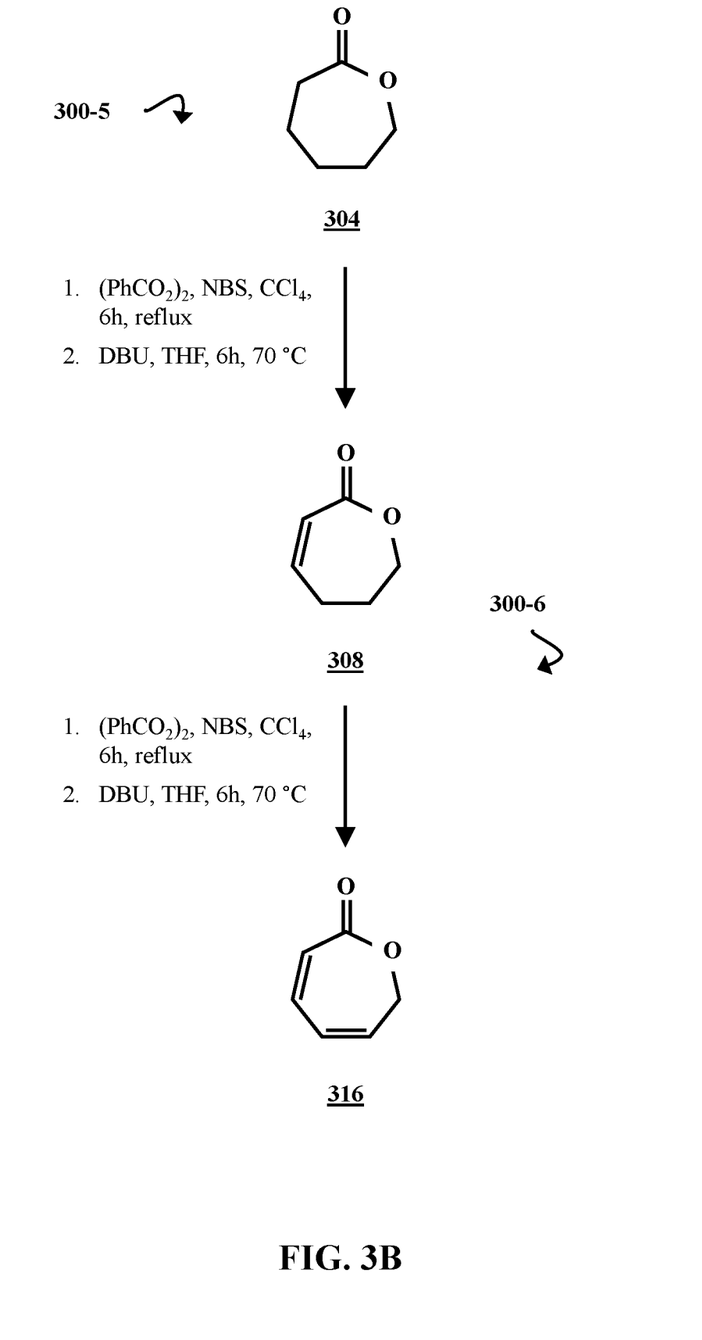
FIG. 3B is a chemical reaction diagram illustrating additional processes of synthesizing unsaturated caprolactones, according to some embodiments of the present disclosure.

FIG. 3B is a chemical reaction diagram illustrating additional processes 300-5 and 300-6 of synthesizing the unsaturated caprolactones 308 and 316, according to some embodiments of the present disclosure. In the first step of process 300-5, caprolactone is combined with benzoyl peroxide (($PhCO_2)_2$) and N-bromosuccinimide (NBS) in carbon tetrachloride ($CCl_4$), and the mixture is refluxed for approximately six hours. In the second step of process 300-5, 1,8-diazabicyclo[5.4.0]undec-7-ene (DBU) is combined with the product of the first step of a tetrahydrofuran (THF) solution. This solution is reacted at approximately 70° C. for about three hours, and produces the α,β-unsaturated caprolactone 308. In process 300-6, the two steps of process 300-5 are repeated with the α,β-unsaturated caprolactone 308 taking the place of caprolactone 304. This reaction produces the di-unsaturated caprolactone 316.

Figure 4A:
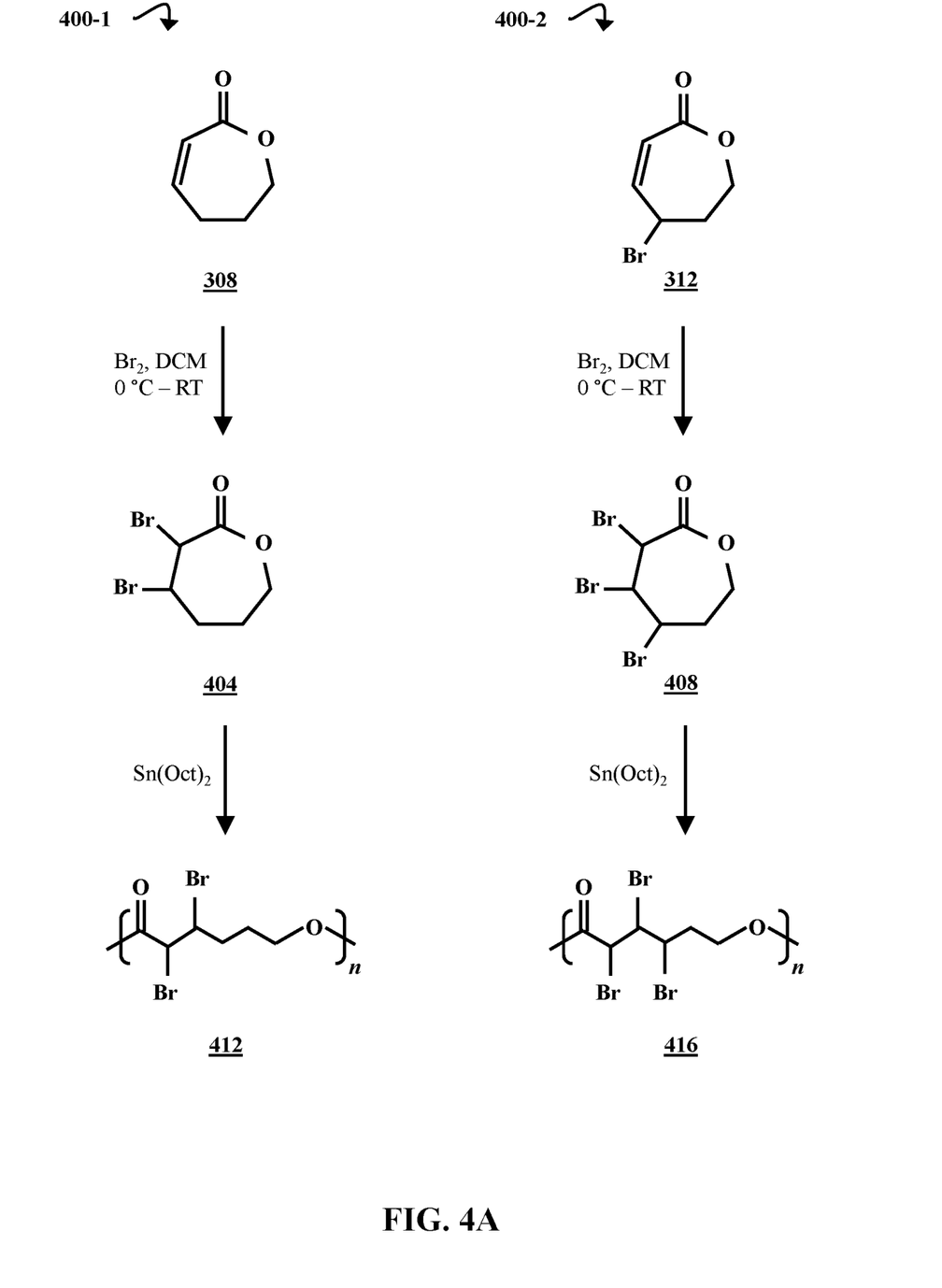
FIG. 4A is a chemical reaction diagram illustrating processes of synthesizing two bromine-substituted polycaprolactone polymers, according to some embodiments of the present disclosure.

FIG. 4A is a chemical reaction diagram illustrating processes 400-1 and 400-2 of synthesizing two bromine-substituted polycaprolactone polymers 412 and 416, according to some embodiments of the present disclosure. Processes 400-1 and 400-2 are carried out under substantially similar conditions. In the first steps of processes 400-1 and 400-2, respectively, the α,β-unsaturated caprolactone 308 and the bromo-caprolactone 312 are reacted with bromine ($Br_2$) in dichloromethane (DCM) at a temperature ranging from about 0° C. to about 27° C. The first step of process 400-1 produces a dibromo-caprolactone 404, and the first step of process 400-2 produces a tribromo-caprolactone 408.

In the second steps of processes 400-1 and 400-2, respectively, the polybromo-caprolactones 404 and 408 are reacted in a ring-opening polymerization with stannous octoate ($Sn(Oct)_2$) to produce bromine-substituted polycaprolactone polymers 412 and 416. The reaction between the dibromo-caprolactone 404 and $Sn(Oct)_2$ produces a polycaprolactone polymer 412 with two bromine substituents per repeat unit, and the reaction between the tribromo-caprolactone 408 and $Sn(Oct)_2$ produces a polycaprolactone polymer 416 with three bromine substituents per repeat unit. Ring-opening polymerizations are discussed in greater detail with respect to FIG. 1.

Figure 4B:
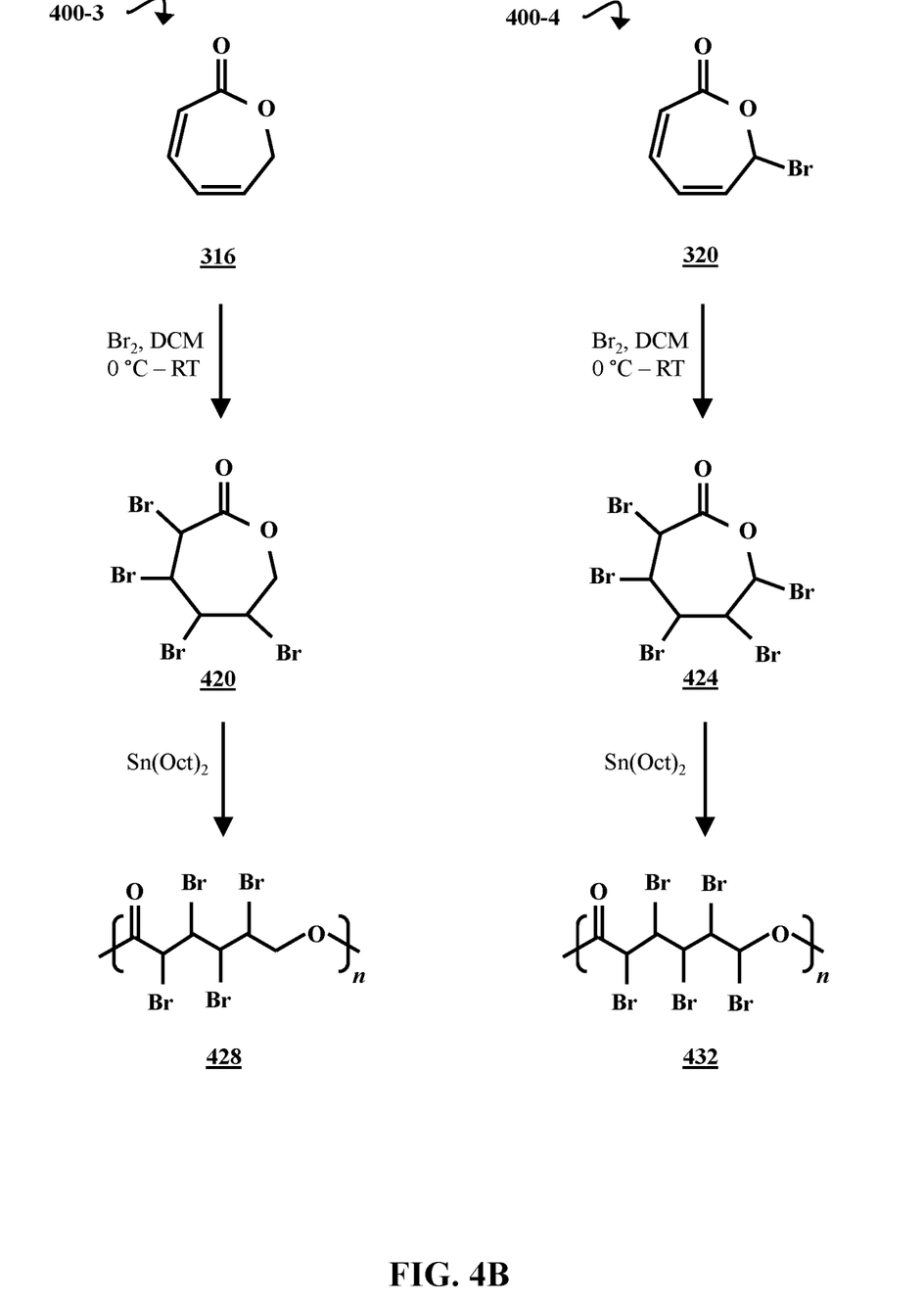
FIG. 4B is a chemical reaction diagram illustrating processes of forming two additional bromine-substituted polycaprolactone polymers, according to some embodiments of the present disclosure.

FIG. 4B is a chemical reaction diagram illustrating processes 400-3 and 400-4 of forming two additional bromine-substituted polycaprolactone polymers 428 and 432, according to some embodiments of the present disclosure. Processes 400-3 and 400-4 are carried out under substantially similar conditions. In the first steps of processes 400-3 and 400-4, respectively, the di-unsaturated caprolactone 316 and the di-unsaturated bromo-caprolactone 320 are reacted with bromine ($Br_2$) in dichloromethane (DCM) at a temperature ranging from about 0° C. to about 27° C. The first step of process 400-3 produces a tetrabromo-caprolactone 420, and the first step of process 400-2 produces a pentabromo-caprolactone 424.

In the second steps of processes 400-3 and 400-4, respectively, the polybromo-caprolactones 420 and 424 are reacted in a ring-opening polymerization with stannous octoate ($Sn(Oct)_2$) to produce bromine-substituted polycaprolactone polymers 428 and 432. The reaction between the tetrabromo-caprolactone 420 and $Sn(Oct)_2$ produces a polycaprolactone polymer 428 with four bromine substituents per repeat unit, and the reaction between the pentabromo-caprolactone 424 and $Sn(Oct)_2$ produces a polycaprolactone polymer 432 with five bromine substituents per repeat unit.

Figure 4C:
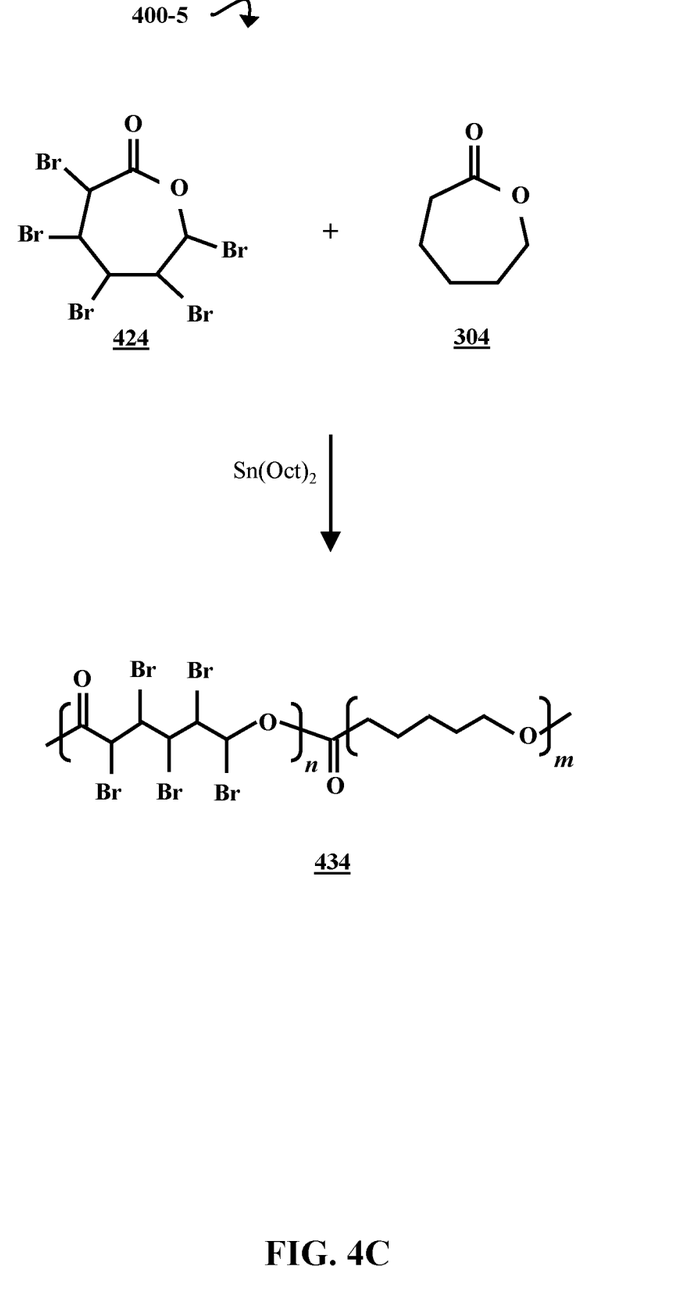
FIG. 4C is a chemical reaction diagram illustrating a process of polymerizing a pentabromo-caprolactone with non-functionalized caprolactone, according to some embodiments of the present disclosure.

FIG. 4C is a chemical reaction diagram illustrating a process 400-5 of polymerizing a pentabromo-caprolactone 424 with non-functionalized caprolactone 304, according to some embodiments of the present disclosure. In this reaction, a combination of the pentabromo-caprolactone 424 and non-functionalized caprolactone 304 are reacted with stannous octoate ($Sn(Oct)_2$) in a ring-opening polymerization reaction. The reaction produces a polycaprolactone polymer having repeat units (n) with five bromine substituents, as well as non-functionalized repeat units (m). The ratio of m to n portions of the polycaprolactone polymer 434 is determined by the ratio of pentabromo-caprolactone monomers 424 to caprolactone 304 used in the polymerization. Each of the multifunctionalized polycaprolactone polymerizations can occur in combination with caprolactone 304 to provide non-functionalized repeat units, though these reactions are not illustrated herein.

Figure 4D:
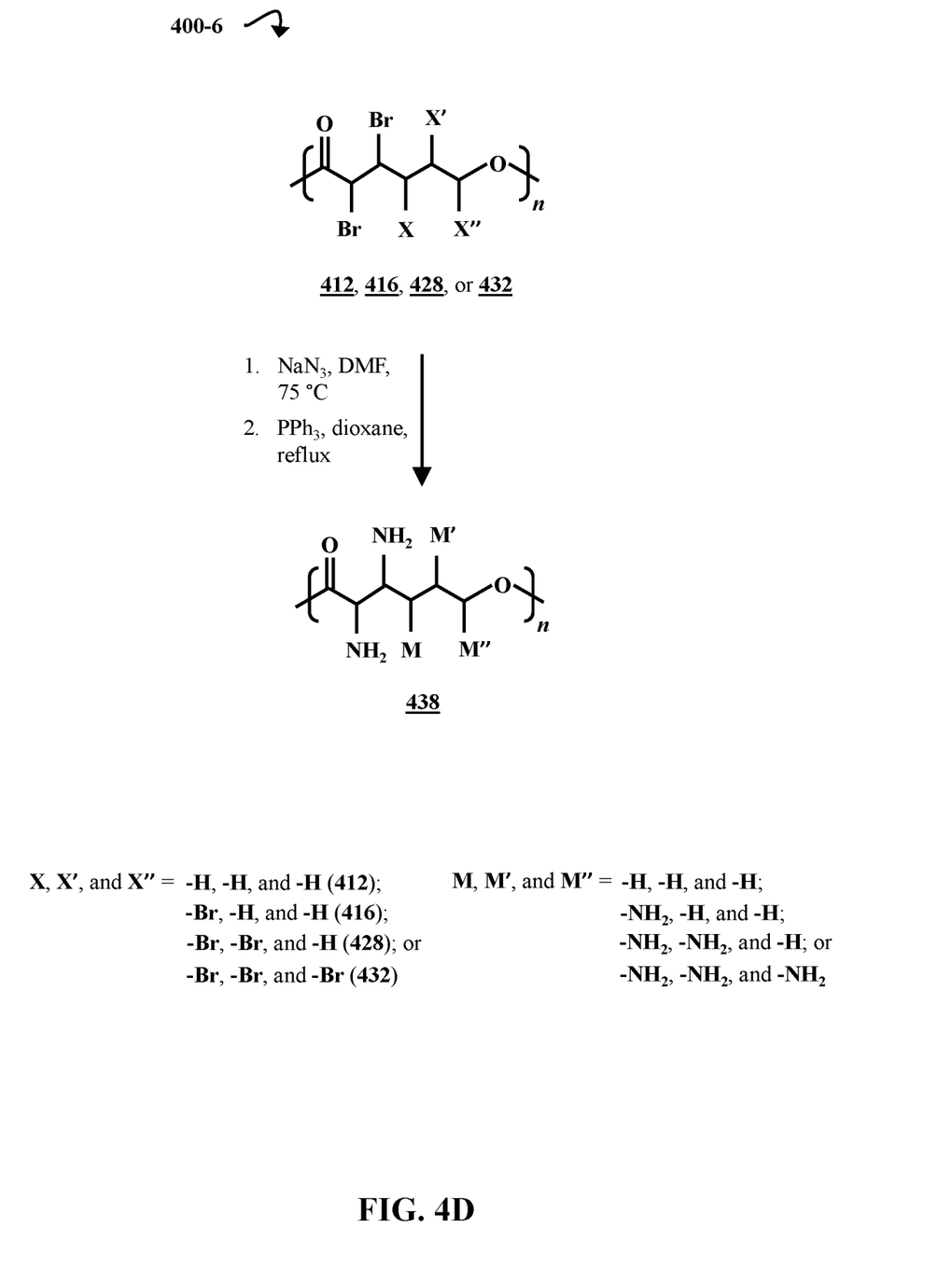
FIG. 4D is a chemical reaction diagram illustrating a process of forming an amino-substituted polycaprolactone polymer, according to some embodiments of the present disclosure.

FIG. 4D is a chemical reaction diagram illustrating a process 400-6 of forming an amino-substituted polycaprolactone polymer 438, according to some embodiments of the present disclosure. Process 400-6 replaces bromine substituents on the brominated polycaprolactone polymers 412, 416, 428, and 432 with primary amino functional groups ($—NH_2$). In FIG. 4D, the bromine and hydrogen atom substituents are represented by X, X', and X". In the first step of process 400-6, a brominated polycaprolactone polymer 412, 416, 428, or 432 is reacted with sodium azide in a dimethylformamide (DMF) solution at approximately 75° C. In the second step of process 400-6, the product of the first step is combined with triphenylphosphine and dioxane and refluxed to produce a multifunctionalized polycaprolactone polymer 438 with primary amino functional groups. The number of amino groups per repeat unit of the multifunctionalized polycaprolactone polymer 438 depends upon the number of bromine substituents per repeat unit of the polycaprolactone polymer 412, 416, 428, or 432 used as a starting material. The hydrogen atoms and amino functional groups on the multifunctionalized polycaprolactone polymer 438 are represented by M, M', and M" in FIG. 4D.

Figure 5A:
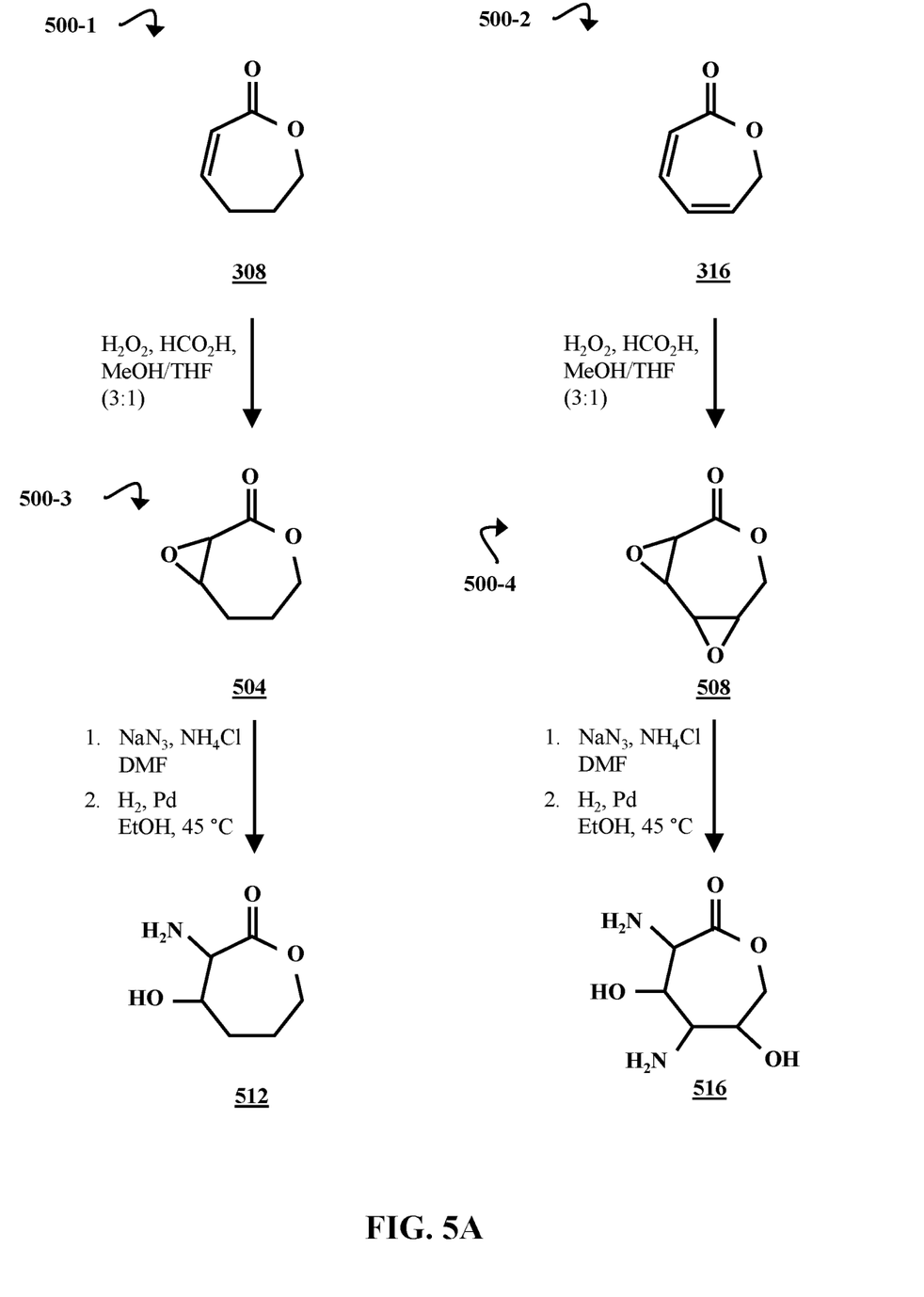
FIG. 5A is a chemical reaction diagram illustrating processes of forming amino- and hydroxyl-substituted caprolactones, according to some embodiments of the present disclosure.

FIG. 5A is a chemical reaction diagram illustrating processes 500-1, 500-3, 500-2 and 500-4 of forming amino- and hydroxyl-substituted caprolactones 512 and 516, according to some embodiments of the present disclosure. Processes 500-1 and 500-2 are carried out under substantially similar conditions. In processes 500-1 and 500-2, respectively, the α,β-unsaturated caprolactone 308 and the di-unsaturated caprolactone 316 are reacted with hydrogen peroxide ($H_2O_2$) and formic acid ($HCO_2H$) in an approximately 3:1 mixture of methanol (MeOH) and tetrahydrofuran (THF). Process 500-1 produces 3,8-dioxabicyclo[5.1.0]octan-2-one 504, and process 500-2 produces 3,6,9-trioxatricyclo[6.1.0.0$^{2,4}$]nonan-5-one 508.

In the second steps of processes 500-3 and 500-4, respectively, the epoxide groups on 3,8-dioxabicyclo[5.1.0]octan-2-one 504, and 3,6,9-trioxatricyclo[6.1.0.0$^{2,4}$]nonan-5-one 508 are opened in a reaction with sodium azide ($NaN_3$). These epoxide-opening reactions are carried out in a mixture of ammonium chloride ($NH_4Cl$) and dimethylformamide (DMF). The azido groups formed in this step are then reduced in a palladium (Pd) catalyzed reaction with hydrogen gas ($H_2$). The reduction reactions take place in ethanol (EtOH) at approximately 45° C. In process 500-3, the reaction forms a difunctionalized caprolactone (3-amino-4-hydroxyoxepan-2-one) 512, and in process 500-4, the reaction forms a tetrafunctionalized caprolactone (3,5-diamino-4,6-dihydroxyoxepan-2-one) 516.

Figure 5B:
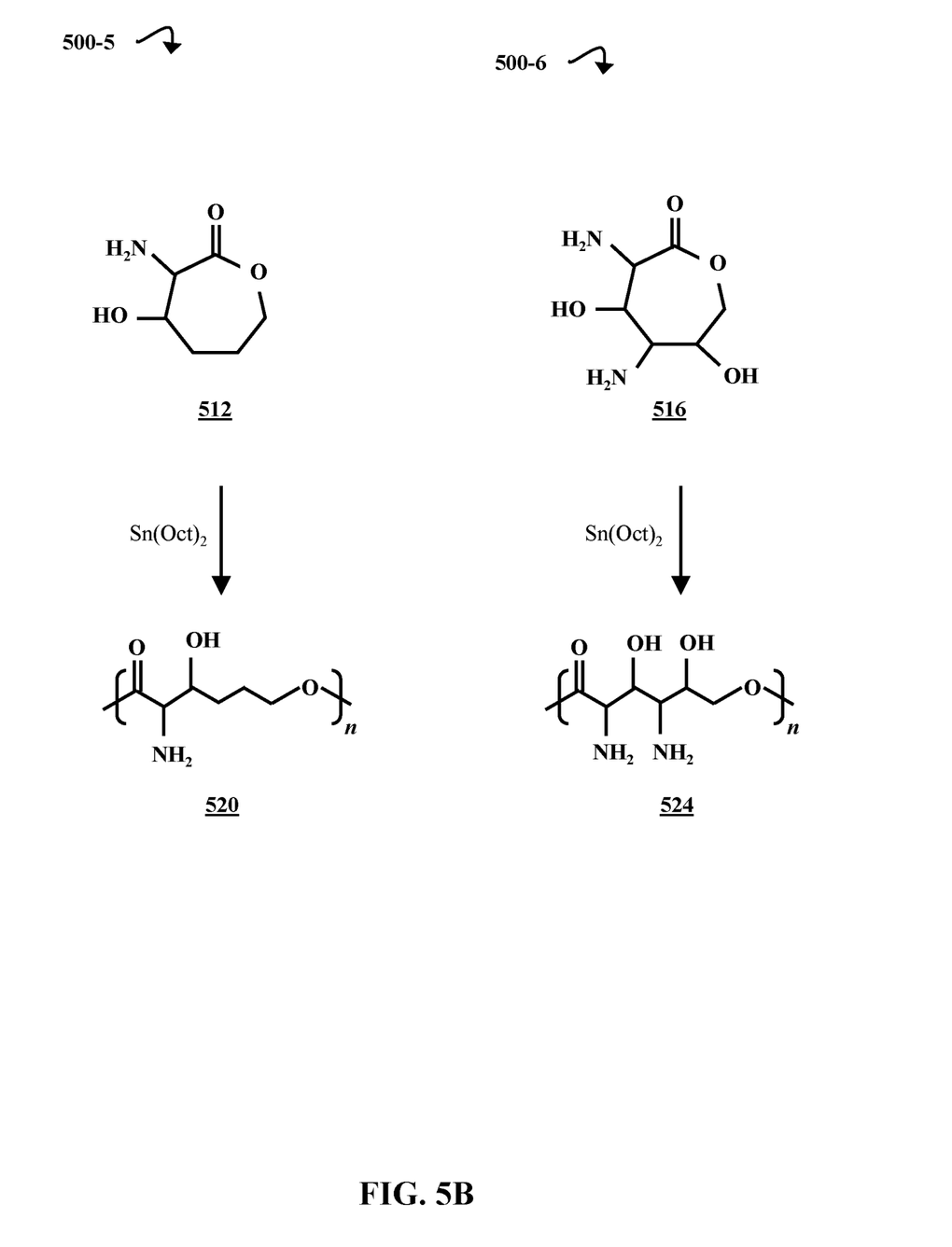
FIG. 5B is a chemical reaction diagram illustrating processes of forming amino- and hydroxyl-substituted multifunctionalized polycaprolactones, according to some embodiments of the present disclosure.

FIG. 5B is a chemical reaction diagram illustrating processes 500-5 and 500-6 of forming amino- and hydroxyl-substituted multifunctionalized polycaprolactones 520 and 524, according to some embodiments of the present disclosure. In processes 500-5 and 500-6, respectively, the difunctionalized caprolactone 512 and the tetrafunctionalized caprolactone 524 are reacted with stannous octoate (Sn(Oct)$_2$) in ring-opening polymerization reactions. The reaction with the difunctionalized caprolactone 512 produces a multifunctionalized polycaprolactone polymer 520 with two functional groups (an amino group and a hydroxyl group) per repeat unit, and the reaction with the tetrafunctionalized caprolactone 516 produces a multifunctionalized polycaprolactone polymer 524 with four functional groups (two amino groups and two hydroxyl groups) per repeat unit. The ring-opening polymerizations can also be carried out with a mixture of multifunctionalized polycaprolactones (e.g., polycaprolactones 438, 520, and 524) and non-functionalized caprolactone 304 in order to provide variable control over the degree of functionalization. This is discussed in greater detail with respect to FIG. 4C.

Figure 6:
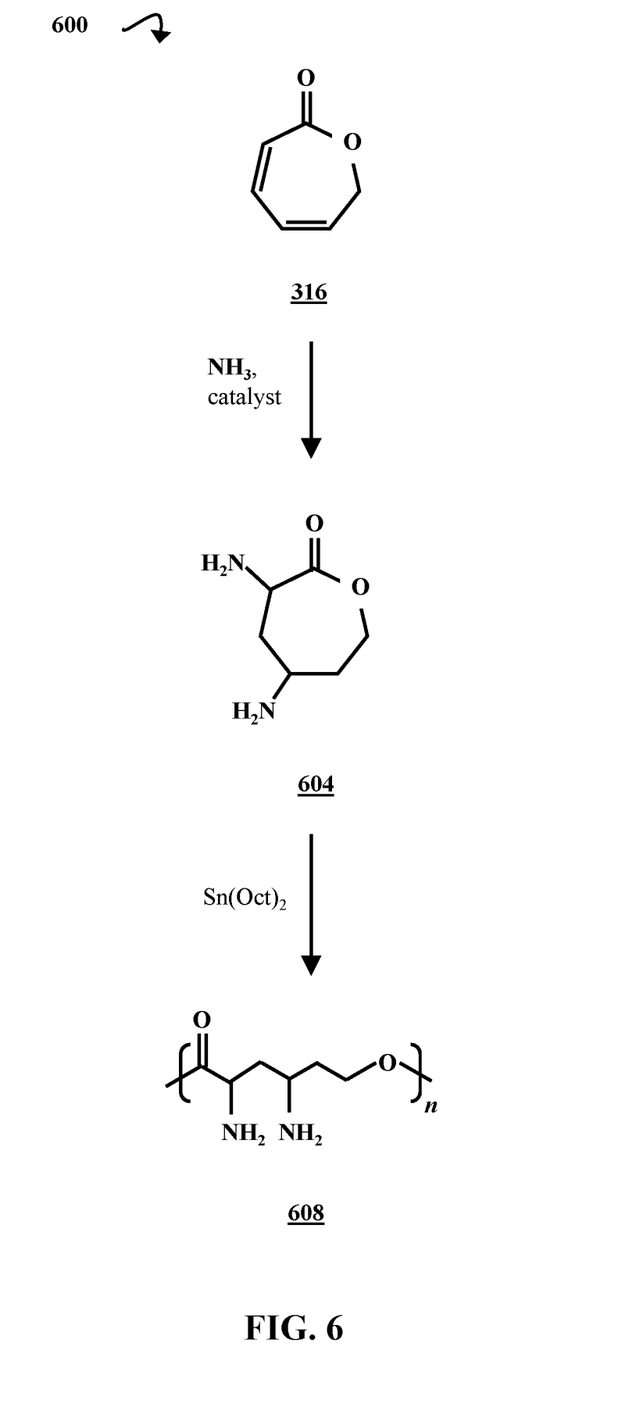
FIG. 6 is a chemical reaction diagram illustrating a process of forming a multifunctionalized polycaprolactone polymer by hydroamination, according to some embodiments of the present disclosure.

FIG. 6 is a chemical reaction diagram illustrating a process 600 of forming a multifunctionalized polycaprolactone polymer 608 by hydroamination, according to some embodiments of the present application. In the first step in process 600, di-unsaturated caprolactone 316 is reacted with ammonia ($NH_3$) and a hydroamination catalyst (e.g., calcium, aluminum, indium, bismuth, zeolites, etc.). This reaction produces a di-amino caprolactone 604. The di-amino caprolactone 604 is reacted in a ring-opening polymerization with stannous octoate ($Sn(Oct)_2$) to produce a polycaprolactone polymer having two amino groups per repeat unit 608. The two amino groups on this polycaprolactone 608 are in the L and M positions illustrated in FIG. 2, and the L', M', and M" positions are non-functionalized. It should be noted that, in some embodiments, ammonia can be replaced with a primary amine (i.e., an amine compound wherein one of the three hydrogen atoms in ammonia has been replaced by a substituted or unsubstituted alkyl or aromatic group), providing an additional substituent, bound to the nitrogen atom in the amine, to the caprolactone. Examples of primary amines that can be used can include methylamine, aniline, amino acids, tris(hydroxymethyl)aminomethane, allyl amine, etc.

Figure 7:
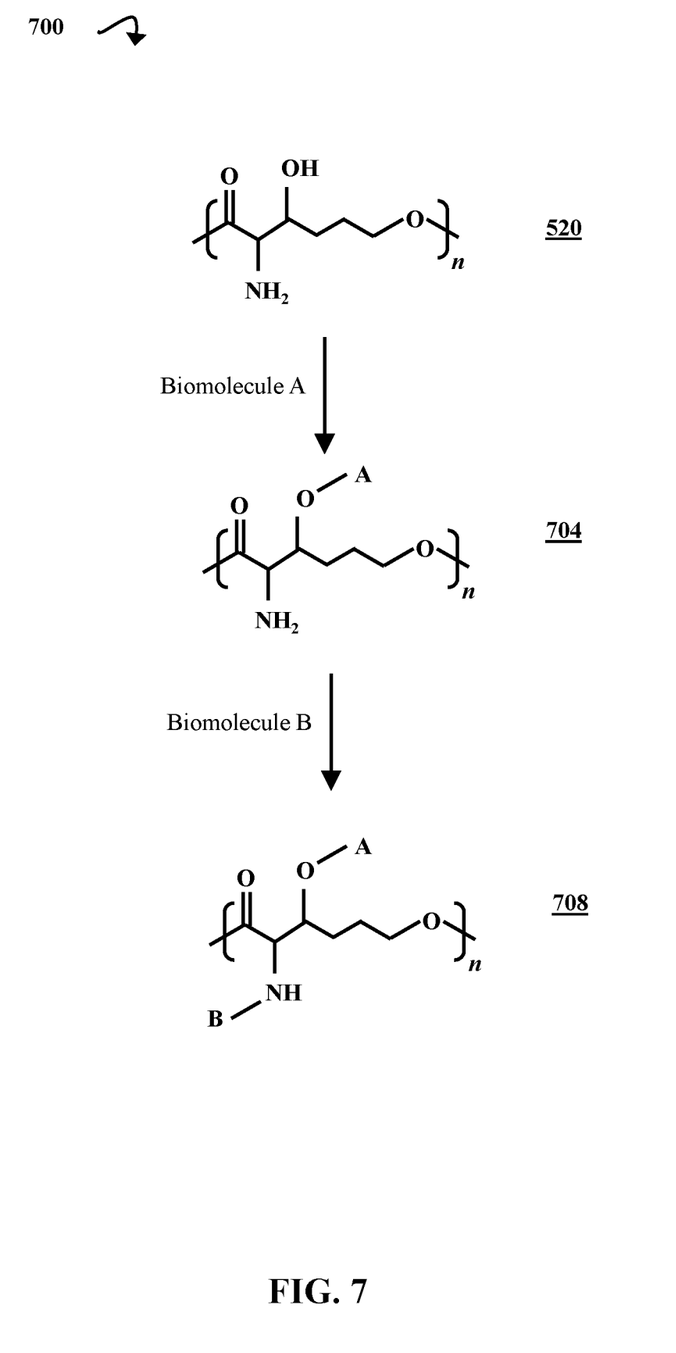
FIG. 7 is a chemical reaction diagram illustrating a generic process of binding a first biomolecule to a multifunctionalized polycaprolactone polymer and a second biomolecule to a multifunctionalized polycaprolactone, according to some embodiments of the present disclosure.

FIG. 7 is a chemical reaction diagram illustrating a generic process 700 of binding a first biomolecule to a multifunctionalized polycaprolactone polymer 520 and a second biomolecule to a multifunctionalized polycaprolactone 704, according to some embodiments of the present disclosure. The reaction conditions for the two reactions in process 700 depend upon the selection of biomolecule and the functional group to which it is bonded, as would be understood by one skilled in the art. The polycaprolactone polymer 520 used in process 700 has two different functional groups per repeat unit, an amino group and a hydroxyl group. In the first reaction in this process, the multifunctionalized polycaprolactone 520 is reacted with biomolecule A, which is a biomolecule that binds to the hydroxyl groups on the polycaprolactone 520. Examples of biomolecule A can include Arg-Gly-Asp (RGD) (e.g., RGD binding motifs in fibronectin, integrin, napsin-A (NAPSA), etc.), RGD peptidomimetics, laminin-derived peptides, etc. The reaction with biomolecule A produces a polycaprolactone polymer having one biomolecule and one amino group per repeat unit 704.

In the second reaction, the polycaprolactone polymer 704 produced in the first reaction is reacted with biomolecule B, which binds to the amino groups on the polycaprolactone 520. Examples of biomolecule B can include Lys-Arg-Ser-Arg (KRSR) peptides (SEQ ID NO: 7), Ile-Lys-Val-Ala-Val (IKVAV) peptides (SEQ ID NO: 2), Pro-His-Ser-Arg-Asn (PHSRN) peptides (SEQ ID NO: 8), etc. The reaction with biomolecule B produces a polycaprolactone polymer having two biomolecules per repeat unit 708.

In some embodiments, the biofunctionalized polycaprolactone polymer 708 produced in process 700 is used in tissue engineering. Tissue engineering is a strategy that uses a combination of engineering and materials science methods, scaffolds, cells, and biologically active molecules to improve, repair, and/or replace biological tissue. For example, the biofunctionalized polycaprolactone 708 can form a scaffold that mimics the extracellular matrix of a tissue that is to be grown. The bioactive molecules bound to the polycaprolactone 708 can be biomolecules that encourage cell adhesion, promote cell growth, mimic the structure and properties of the extracellular matrix, etc. Examples of these bioactive compounds are discussed in greater detail above. Further, the polycaprolactone scaffold can be made from any multifunctionalized polycaprolactone 208 disclosed herein. Biomolecules can then be bound to the functional groups on the resulting scaffold.

Additionally, drugs can be transported within an organism inside of drug delivery capsules made from the multifunctionalized polycaprolactone polymers 208 with or without bioactive compounds already bound. These drug delivery capsules are microcapsules or nanospheres (i.e. nanoparticles or nanocapsules with a size range of about 10-1,000 nm). The destination and delivery of these microcapsules or nanospheres can be determined by bioactive compounds bound to the polymer.

Additionally, compounds bound to the polycaprolactone polymer can be used to tune the biodegradability and/or biocompatibility of the polymer. In a drug delivery capsule, this tuning gives greater control over the rate and timing of a drug's release from a microcapsule or nanosphere. Further, tuning the biodegradability of the polymer is useful in designing biodegradable sutures or other medical devices. The biofunctionalized polycaprolactone 708 can also be blended with other polymers in order to tune the biodegradability, biocompatibility, crack-resistance, dye-ability, and/or tissue-adhesion. Examples of these polymers can include cellulose propionate, cellulose acetate butyrate, polylactic acid, polylactic acid-co-glycolic acid, etc.

It should also be noted that the multifunctionalized polycaprolactones disclosed herein can have applications outside of biotechnology. For example, the polycaprolactones can be used in plastic models, repair of plastic parts, 3D printing, etc. The multifunctional polycaprolactone polymers can also be used as an extrusion aid, pigment and/or filler dispersion aid, component of urethanes and block polyesters, etc.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these. Temperature and time ranges indicated herein can include the temperature or time on either end of the range, or any temperature or time between these limits. Further, variations in temperature can occur over the course of a reaction.

The synthetic processes discussed herein and their accompanying drawings are not to be construed as limiting. One skilled in the art would recognize that a variety of synthetic reactions may be used that vary in reaction conditions, components, methods, etc., which ultimately generate one or both of multifunctional polycaprolactone compounds and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A multifunctionalized polycaprolactone homopolymer with a formula of:

wherein L is a first primary amine group;
wherein L' is a first hydroxyl group;
wherein M is a second primary amine group;
wherein M' is selected from the group consisting of a first hydrogen atom, a third primary amine group, and a second hydroxyl group;
wherein M" is selected from the group consisting of a second hydrogen atom and a fourth primary amine group; and
wherein the multifunctionalized polycaprolactone homopolymer is formed by polymerizing a multifunctionalized caprolactone monomer.

2. The multifunctionalized polycaprolactone polymer of claim 1, wherein M' is the third primary amine group and M" is the fourth primary amine group.

3. The multifunctionalized polycaprolactone polymer of claim 1, wherein M' is the second hydroxyl group.

4. The multifunctionalized polycaprolactone homopolymer of claim 1, wherein M' is the first hydrogen atom, and M" is the second hydrogen atom.

5. The multifunctionalized polycaprolactone polymer of claim 1, wherein M' is the first hydrogen atom, and M" is the second hydrogen atom.

6. The multifunctionalized polycaprolactone polymer of claim 1, wherein M' is the third primary amine group, and M" is the second hydrogen atom.

7. The multifunctionalized polycaprolactone polymer of claim 1, wherein M' is the second hydroxyl group, and M" is the fourth primary amine group.

8. An article of manufacture comprising a multifunctionalized polycaprolactone homopolymer with a formula of:

wherein L is a first primary amine group;
wherein L' is a first hydroxyl group;
wherein M is a second primary amine group;
wherein M' is selected from the group consisting of a first hydrogen atom, a third primary amine group, and a second hydroxyl group;
wherein, M" is selected from the group consisting of a second hydrogen atom and a fourth primary amine group; and
wherein the multifunctionalized polycaprolactone homopolymer is formed by polymerizing a multifunctionalized caprolactone monomer.

9. The article of manufacture of claim 8, further comprising at least one bioactive compound bound to the polycaprolactone homopolymer.

10. The article of manufacture of claim 9, wherein the bioactive compound is selected from a group consisting of RGD peptides, YIGSR peptides (SEQ ID NO: 1), IKVAV peptides (SEQ ID NO: 2), fibronectin-derived REDV peptides (SEQ ID NO: 3), collagen I mimetic DGEA peptides (SEQ ID NO: 4), osteopontin-derived SVVYGR peptides (SEQ ID NO: 5), elastin-derived VAPG peptides (SEQ ID NO: 6), a peptidomimetic, galactose, lactose, vascular endothelial growth factor, fibronectin domain III 12-14, bone morphogenetic protein 2, dexamethasone, glycerolphosphate, transforming growth factor beta, and basic fibroblast growth factor.

11. The article of manufacture of claim 8, wherein the article of manufacture is a tissue scaffold.

12. The article of manufacture of claim 8, wherein the article of manufacture is a drug delivery capsule.

13. A process of forming a multifunctionalized polycaprolactone polymer, comprising: polymerizing a caprolactone monomer to form a polymer having the following structure:

wherein L is a first primary amine group;
wherein L' is a first hydroxyl group;
wherein M is a second primary amine group;
wherein M' is selected from the group consisting of a first hydrogen atom, a third primary amine group, and a second hydroxyl group; and
wherein M" is selected from the group consisting of a second hydrogen atom and a fourth primary amine group.

14. The process of claim 13, further comprising reacting the multifunctionalized polycaprolactone polymer with a bioactive compound.

15. The process of claim 14, wherein the bioactive compound is selected from a group consisting of RGD peptides, YIGSR peptides (SEQ ID NO: 1), IKVAV peptides (SEQ ID NO: 2), fibronectin-derived REDV peptides (SEQ ID NO: 3), collagen I mimetic DGEA peptides (SEQ ID NO: 4), osteopontin-derived SVVYGR peptides (SEQ ID NO: 5), elastin-derived VAPG peptides (SEQ ID NO: 6), a peptidomimetic, galactose, lactose, vascular endothelial growth factor, fibronectin domain III 12-14, bone morphogenetic protein 2, dexamethasone, glycerolphosphate, transforming growth factor beta, and basic fibroblast growth factor.

* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Homo sapiens

<400> SEQUENCE: 1

Tyr Ile Gly Ser Arg

<210> SEQ ID NO 2
<211> LENGTH: 5
<212> TYPE: PRT
<213> ORGANISM: Homo sapiens

<400> SEQUENCE: 2

Ile Lys Val Ala Val

<210> SEQ ID NO 3
<211> LENGTH: 4
<212> TYPE: PRT
<213> ORGANISM: Artificial Sequence
<220> FEATURE:
<223> OTHER INFORMATION: Homo sapiens

<400> SEQUENCE: 3

Arg Glu Asp Val

<210> SEQ ID NO 4
<211> LENGTH: 4
<212> TYPE: PRT
<213> ORGANISM: Artificial Sequence
<220> FEATURE:
<223> OTHER INFORMATION: Synthesized

<400> SEQUENCE: 4

Asp Gly Glu Ala

<210> SEQ ID NO 5
<211> LENGTH: 7
<212> TYPE: PRT
<213> ORGANISM: Artificial Sequence
<220> FEATURE:
<223> OTHER INFORMATION: Homo sapiens

<400> SEQUENCE: 5

Ser Val Val Tyr Gly Leu Arg

<210> SEQ ID NO 6
<211> LENGTH: 4
<212> TYPE: PRT
<213> ORGANISM: Artificial Sequence
<220> FEATURE:
<223> OTHER INFORMATION: Homo sapiens

<400> SEQUENCE: 6

Val Ala Pro Gly

<210> SEQ ID NO 7
<211> LENGTH: 4
<212> TYPE: PRT
<213> ORGANISM: Artificial Sequence
<220> FEATURE:
<223> OTHER INFORMATION: Homo sapiens

<400> SEQUENCE: 7

Lys Arg Ser Arg

<210> SEQ ID NO 8
<211> LENGTH: 5
<212> TYPE: PRT
<213> ORGANISM: Artificial Sequence
<220> FEATURE:
<223> OTHER INFORMATION: Homo sapiens

<400> SEQUENCE: 8

Pro His Ser Arg Asn